United States Patent [19]

Webb

[11] Patent Number: 4,893,920
[45] Date of Patent: Jan. 16, 1990

[54] OPTICAL SCANNING SYSTEM AND METHOD INCLUDING CORRECTION FOR CROSS SCAN ERROR

[75] Inventor: Robert H. Webb, Lincoln, Mass.

[73] Assignee: Eye Research Institute of Retina Foundation, Boston, Mass.

[21] Appl. No.: 229,990

[22] Filed: Aug. 9, 1988

[51] Int. Cl.⁴ .............................................. A61B 3/10
[52] U.S. Cl. .................................... 351/221; 351/205
[58] Field of Search ............... 351/205, 211, 212, 221, 351/246

[56] References Cited

U.S. PATENT DOCUMENTS 4,768,873  9/1988  Webb .................................. 351/221

*Primary Examiner*—P. M. Dzierzynski
*Attorney, Agent, or Firm*—Lahive & Cockfield

[57] ABSTRACT

An apparatus and method for correcting cross scan error in a two coordinate optical scanning system where the two scanners are spaced apart in the optical system. An anamorphic lens is positioned between the scanner which is introducing the cross scan error and the second scanner, with the lens being formed and positioned so that the focal length on the coordinate of scan from the first scanner is different from its focal length on the coordinate of scan orthogonal to it. An object lens is placed between the second scanner and the object being scanned. This lens in an ophtalmoscope is the lens of the eye.

13 Claims, 2 Drawing Sheets

OPTICAL SCANNING SYSTEM AND METHOD INCLUDING CORRECTION FOR CROSS SCAN ERROR

BACKGROUND OF THE INVENTION

This invention relates in general to two coordinate optical scanning systems and more particularly to a system and method for correcting cross scan error in such systems.

In the art of optical instruments, it is known to scan a surface to be imaged with a small cross section light beam, collect the light reflected from the illuminated spot and direct it to a detector which provides an output signal varying in time in correlation with the scanning of the illuminated spot across the surface. The detector output can be stored in a permanent storage medium or provided directly to a scanning display device, such as a television raster or a cathode ray tube display. By synchronizing the scanning operation of the illuminating source with the scanning of the display signals, a two dimensional image is produced.

There currently exist a number of systems for scanning a small beam of light or a laser beam over the two coordinates, usually orthogonal, to image the object being scanned. Two examples of instruments which employ such scanners are double scanning ophthalmoscopes and scanning microscopes. One design of such instruments utilizes a rotating multi-faceted polygon to generate the light beam scan along one coordinate, typically the horizontal coordinate, followed by a reflection galvanometer to produce a scan along the other coordinate. One source of error in these instruments arises from the lack of parallelism of the reflecting facets of the polygon. This difference in tilt of the facets along the coordinate orthogonal to the one being scanned produces runout error which appears to the instrument as an error in vertical scan. In single scanning systems this error has been corrected by means of a focusing element placed after the scanner which focuses the beam along this orthogonal coordinate at the surface of the object to be imaged, thus eliminating at the object the positional error otherwise introduced. However, in a two-coordinate scanning system this compensation cannot be made because to do so would remove the vertical scanning process itself.

SUMMARY OF THE INVENTION

Broadly speaking the present invention provides an apparatus and method for correcting cross scan error in a two coordinate optical scanning system where the two scanners are spaced apart in the optical system. This is accomplished by including an anamorphic lens between the scanner which is introducing the cross scan error and the second scanner, with the lens being formed and positioned so that the focal length on the coordinate of scan from the first scanner is different from its focal length on the coordinate of scan orthogonal to it. Between the second scanner and the object being scanned, there is an object lens, which in an ophthalmoscope is the lens of the eye. Using this system the cross scan error introduced by the first scanner is, in effect, converted into an angular error and does not, therefore, result in a positional error at the object surface being scanned This anamorphic lens may, for example, be a toric lens or could even be a spherical lens tilted along one axis.

DESCRIPTION OF PREFERRED EMBODIMENTS

Figure 1:
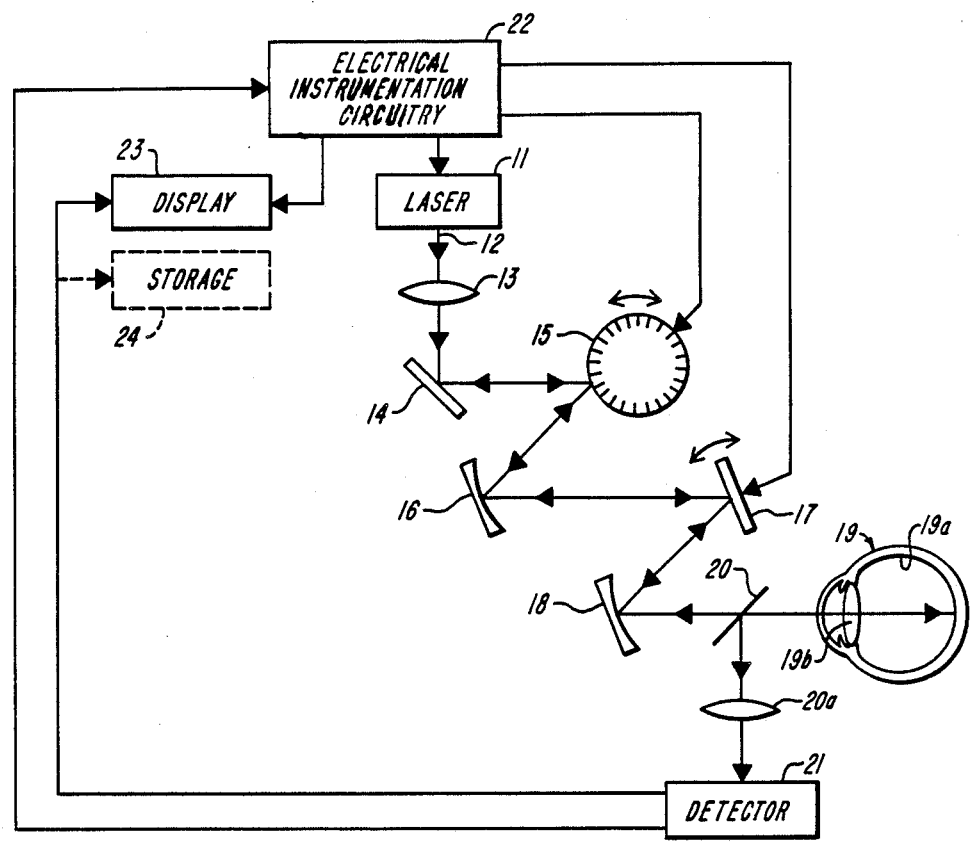
FIG. 1 is an illustration generally in block diagrammatic form of a preferred embodiment of the invention.

FIG. 1 is an illustration of an ophthalmoscope employing the error correction system of this invention. The ophthalmoscope includes a laser source 11 which passes a laser beam 12 through a beam shaping lens 13 to a turning mirror 14 which redirects the beam onto the facets of a multi-faceted rotating polygon 15 to provide the horizontal scanning action. The scanned output beam from the rotating polygon 15 is focused by an anamorphic lens or mirror 16 having a longer focal length on the vertical coordinate than its focal length on the coordinate normal to the scanned coordinate. A suitable form for this anamorphic lens is a toric lens. While in the description below various elements are usually referred to as a lens, it would be at least equally probable that a mirror would be used for such a function. Accordingly it should be understood that use of lens is intended also to connote an equivalent focus mirror.

The output from the anamorphic lens 16 is directed toward a second scanning element 17, typically a reflecting galvanometer mirror which provides for vertical scanning motion and which is positioned to be approximately at the image point on the horizontal coordinate of the anamorphic lens 16. This vertical scanning element 17 is followed by a spherical lens or mirror 18 which is placed so that element 17 is conjugate to pupil 19b. The reflected beam from the fundus 19a reaches a detector 21, after some optical processing, most simply by beam splitter 20 and lens 20a. Control circuitry 22 provides for coordination of the scanning motions of the two scanners with the raster scan of display device 23.

FIG. 1 illustrates a system in which the light reflector from the fundus is reflected from the beam splitter 20, typically a half silvered mirror, through lens 20a to the detector 21.

The correction system of this invention can also be employed with a confocal optical system in which the reflected light from the fundus 19a is passed back along the same optical path as the input beam. In this configuration the beam separator 20 is advantageously placed between the lens 13 and the turning mirror 14.

Figure 2:
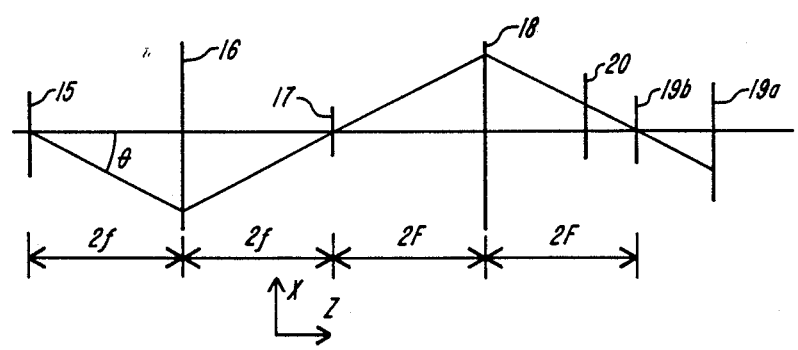
FIG. 2 is a ray diagram in the horizontal plane of a correction system in accordance with this invention.

FIG. 2 is a ray diagram pictured along the horizontal coordinate of the scan of the ophthalmoscope system illustrated in FIG. 1. Only the horizontal scan lines are illustrated.

In FIG. 2, 19a is the retina and 19b is the eye pupil. At this pupil is the first (objective) lens of the optical system. This objective is the cornea and crystalline lens in the human eye, or a standard object in a traditional microscope. The horizontal scanner 15 is, along this horizontal coordinate, an optical conjugate to the eye pupil 19b. The anamorphic element 16 is a positive toric mirror, with a focal length f along the horizontal coordinate. Accordingly it focuses light in this plane from the facets of the horizontal scanner 15 approximately onto the reflecting face of the vertical scanner 17. The beam from the vertical scanner 17 is relayed by the symmetrical spherical mirror 18 to a focal point on the optical axis at the lens 19b and thence passes to the retina surface 19a. FIG. 2 shows the deviation in the horizontal plane, where there is no error correction required and the optics operate as a conventional two coordinate optical scanner.

Figure 3A:
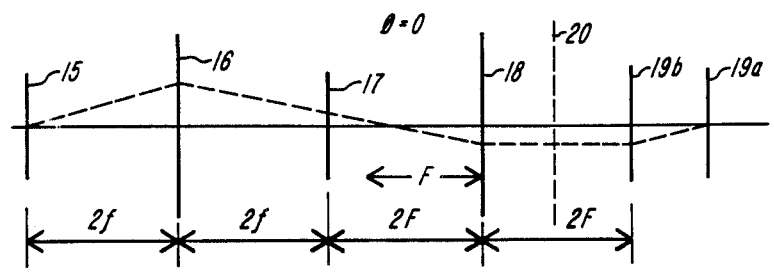
FIGS. 3a and 3b are is a ray diagram in the vertical plane of a correction system in accordance with the principles of this invention.
Figure 3B:
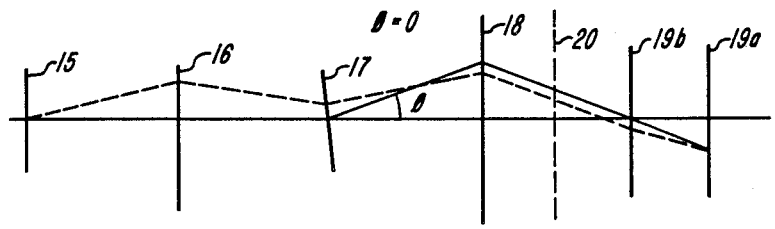

In FIGS. 3a and 3b there are illustrated the same optical system shown in the vertical plane. The positive symmetrical mirror 18 conjugates the lens image at 19b to the vertical scanner 17. The dotted line shows the cross scan effect as it should be corrected (at the instant when $\phi=0$ for convenience). However, the vertical focal length of element 16 is now longer than f and hence the focal point from the horizontal rotating element 15 lies beyond the vertical reflection element 17. This cross scan ray is then relayed by mirror 18 in a substantially parallel direction onto an off axis point of the lens 19b and focussed on the retina at the optical axis representing the zero scan angle.

The solid line in FIG. 3b shows the desired vertical deflection through a nonzero defection angle $\phi$. The dot-dash line in FIG. 3b represents the ray diagram for the vertical cross scan error, when the vertical deflection angle is not zero. As illustrated, this ray is incident on the pupil 19b at an angle such that it is focussed on the retina at the same point as the ideal curve for the vertical scan angle $\phi$.

If the focal length in the symmetrical mirror 18 is F and if f=F, then the focal length of mirror 16 in the vertical direction is 6f/5 and in the horizontal direction is f. Thus there is introduced approximately a 20% difference in focal length to achieve this correction. This can be accomplished, not only by a toric lens, but also by tilting a spherical mirror on its vertical axis, by a spherical lens plus a cylindrical lens.

Figure 4:
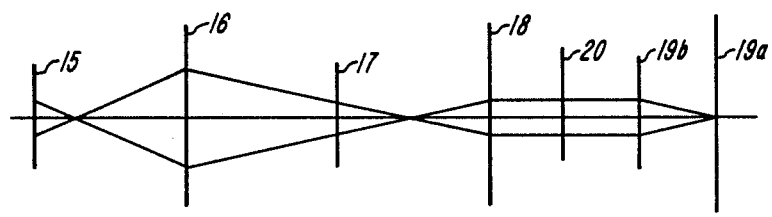
FIGS. 4 and 5 are beam diagrams of the system of FIG. 1.
Figure 5:
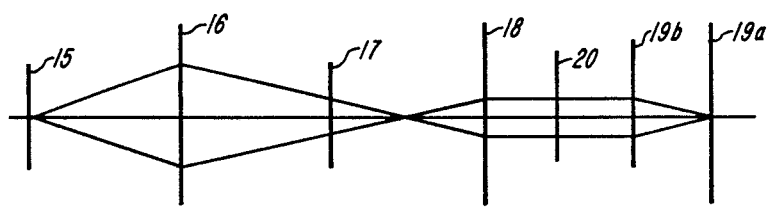

FIGS. 4 and 5 illustrate the envelope of the laser beam in the horizontal and in the vertical plane. It can be seen that the beam focus pattern is the same for both the vertical and the horizontal coordinate from toric mirror 16 to the fundus. The effect of the the toric lens 16 on the beam shape not the envelope or pattern is to render it asymmetrical. In order to correct this beam asymmetry an anamorphic beam shaping lens 13 is placed between the laser source 11 and the horizontal scanner 15, focusing the beam at the horizontal scanner 15 in the vertical plane and at a point beyond the horizontal scanner in the horizontal plane. This correction can, for example, be accomplished with cylindrical lenses.

In one commercially available rotating polygon the run out error introduced by the lack of parallelism is cited as ±30 seconds, and the sum of these deviations is 60 seconds=1 minarc=1/60th of a degree. If the raster is, for example, 25 degrees, then the sum of all of the deviations equals 1500 seconds, or ½ of a pixel. Such an error would be visually observable as a bunching of raster lines.

With the cross scan error correction system described, this visual effect is substantially removed, indicating that the sum of the deviations left after correction is less than 1/30 pixel.

While the embodiment described has been for a scanning ophthalmoscope it will be appreciated that the same principles apply to other two coordinate scan systems such as scanning microscopes.

What is claimed is:

1. An optical scanning system for scanning an object through an objective lens comprising,
    a laser source for generating a beam of laser light,
    an anamorphic beam shaping element placed to intercept said laser beam and provide a specific asymmetrical cross sectional shape to said laser beam,
    a first scanning element in the form of a rotating polygon having a plurality of reflecting facets positioned to receive said laser beam from said beam shaping element and scan said beam along a first coordinate;
    a second scanning element positioned to receive said laser beam from said first scanning element and scan it along a coordinate normal to said first coordinate onto said objective lens to a focus on said object;
    a spherical mirror and lens characterized by a first focal length and position on the optical axis of said system in a plane normal to the axis of said system to focus light impingement upon it onto said objective lens,
    an anamorphic focusing element positioned between said first scanning element and said second scanning element, said anamorphic focusing element having a focal length along said first coordinate such that it focuses the image along the first coordinate from said first scanning element at approximately the plane of said second scanning element, said anamorphic focusing element having a focal length along said second coordinate such that it focuses the image of said first scanning element at a point substantially beyond the plane of said second scanning element.

2. An optical scanning system in accordance with claim 1 wherein said beam shaping element shapes the laser beam incoming to said first scanning element such that its passage through said anamorphic focusing element produces a substantially symmetrical beam thereafter.

3. An optical scanning system in accordance with claim 1 wherein said object to be scanned is the fundus of an eye and the objective lens is the lens of said eye.

4. An optical scanning system in accordance with claim 1 wherein said anamorphic focusing element is a toric lens.

5. An optical scanning system in accordance with claim 1 wherein said second scanning element is a deflection galvanometer.

6. An optical scanning system in accordance with claim 1 wherein said beam shaping element includes a cylindrical lens.

7. An optical scanning system in accordance with claim 1 wherein said anamorphic focusing element is a spherical mirror tilted along one of said axes.

8. A method for optically scanning an object through an objective lens comprising the steps of,
    generating a beam of laser light,
    shaping said laser beam to provide a specific cross sectional shape to said laser beam,
    transmitting said shaped laser beam onto the reflecting facets of a first scanning element in the form of a rotating polygon having a plurality of reflecting facets positioned to receive said laser beam and scan said beam along a first coordinate;

positioning a second scanning element to receive said laser beam from said first scanning element and scan it along a coordinate normal to said first coordinate onto said objective lens to a focus on said object;

positioning a spherical mirror between said second scanning element and said object lens on the optical axis of said system in a plane normal to the axis of said system to focus light impingement upon it from said second scanning element onto said objective lens, positioning an anamorphic focusing element between said first scanning element and said second scanning element, said focusing element having a focal length along said first coordinate such that it focuses the image along the first coordinate from said first scanning element at approximately the plane of said second scanning element, said anamorphic focusing element having a focal length along said second coordinate such that it focuses the image from said first scanning element at a point substantially beyond the plane of said second scanning element.

9. A method in accordance with claim 8 wherein said laser beam is shaped such that its passage through said anamorphic focusing element produces a substantially symmetrical beam thereafter.

10. A method in accordance with claim 8 wherein said object to be scanned is the fundus of an eye and the objective lens is the lens of said eye.

11. A method in accordance with claim 8 wherein said anamorphic focusing element is a toric lens.

12. A method in accordance with claim 8 wherein said second scanning element is a deflection galvanometer.

13. A method in accordance with claim 8 wherein said anamorphic focusing element is a spherical mirror tilted along one of said axes.

* * * * *